(12) United States Patent
Tao et al.

(10) Patent No.: US 7,037,554 B2
(45) Date of Patent: May 2, 2006

(54) MOISTURE SENSOR BASED ON EVANESCENT WAVE LIGHT SCATTERING BY POROUS SOL-GEL SILICA COATING

(75) Inventors: Shiquan Tao, Starkville, MS (US); Jagdish P. Singh, Starkville, MS (US); Christopher B. Winstead, Hattiesburg, MS (US)

(73) Assignee: Mississippi State University, Mississippi State, MS (US)

(*) Notice: Subject to any disclaimer, the term of this patent is extended or adjusted under 35 U.S.C. 154(b) by 126 days.

(21) Appl. No.: 10/608,228

(22) Filed: Jun. 30, 2003

(65) Prior Publication Data

US 2004/0264901 A1 Dec. 30, 2004

(51) Int. Cl.
*B05D 5/06* (2006.01)
*G02B 6/02* (2006.01)

(52) U.S. Cl. .................. 427/163.2; 427/163.1; 427/299; 427/314; 427/398.1

(58) Field of Classification Search .......... 427/163.1, 427/163.2, 245, 246, 299, 307, 314, 398.1; 250/227.11, 227.14; 385/12, 123, 126, 128, 385/144; 65/440, 448, 473
See application file for complete search history.

(56) References Cited

U.S. PATENT DOCUMENTS

| 4,634,856 | A |   | 1/1987 | Kirkham |
|---|---|---|---|---|
| 4,894,532 | A |   | 1/1990 | Peterson et al. |
| 5,040,090 | A |   | 8/1991 | Birkle et al. |
| 5,319,975 | A |   | 6/1994 | Pederson et al. |
| 5,637,507 | A | * | 6/1997 | Wicks et al. ............. 436/166 |
| 6,241,948 | B1 | * | 6/2001 | Watkins et al. ........ 422/82.05 |
| 6,623,977 | B1 | * | 9/2003 | Farquharson et al. ..... 436/164 |
| 6,810,184 | B1 | * | 10/2004 | Skutnik .................... 385/123 |
| 6,819,811 | B1 | * | 11/2004 | Goldstein .................. 385/12 |
| 2002/0041724 | A1 | * | 4/2002 | Ronnekleiv et al. ....... 385/12 |
| 2002/0182740 | A1 | * | 12/2002 | Noire et al. ............... 436/106 |

FOREIGN PATENT DOCUMENTS

JP 63-265140 A * 11/1988
JP 01-193628 A * 8/1989

OTHER PUBLICATIONS

Badini et al., "Sol-gels with fiber-optic chemical sensor potential: Effects of preparation, aging, and long-term storage", Rev. Sci. Instrum. 66 (8), pp. 4034-4040, Aug. 1995.*

(Continued)

*Primary Examiner*—Timothy Meeks
*Assistant Examiner*—Wesley D. Markham
(74) *Attorney, Agent, or Firm*—DLA Piper Rudnick; Gray Cary US LLP

(57) ABSTRACT

An optical fiber moisture sensor that can be used to sense moisture present in gas phase in a wide range of concentrations is provided, as well techniques for making the same. The present invention includes a method that utilizes the light scattering phenomenon which occurs in a porous sol-gel silica by coating an optical fiber core with such silica. Thus, a porous sol-gel silica polymer coated on an optical fiber core forms the transducer of an optical fiber moisture sensor according to an embodiment. The resulting optical fiber sensor of the present invention can be used in various applications, including to sense moisture content in indoor/outdoor air, soil, concrete, and low/high temperature gas streams.

20 Claims, 12 Drawing Sheets

Light source — Porous sol-gel silica coating — Photodetector

OTHER PUBLICATIONS

Raj, A.M. Edwin Suresh, et al., "Zinc(ii) oxide-zinc(II) molybdate composite humidity sensor", Sensors and Actuators B 81, 229-236 (2002).

Hypszer, Ryszaed, et al., "Fiber optic technique for relative humidity sensors", SPIE vol. 3054, 145-150 (1997).

Jindal, Rajeev, et al., "High dynamic range fiber optic relative humidity sensor", Optical Engineering, vol. 41, (5) 1093-1096 (2002).

Khijwania, S.K., et al., "Fiber optic evanescent field absorption sensor: Effect of fiber parameters and geometry of the probe", Optical and Quantum Electronics 31: 625-636, (1999).

Tao, Shiquan, et al., "Porous solgel fiber as a transducer for highly sensitive chemical sensing", Optics Letters, vol. 27, No. 16, 1382-1384, Aug. 15, 2002.

Messica, A., et al,. "Theory of fiber-optic, evanescent-wave spectroscopy and sensors", Applied Optics, vol. 35, No. 13, 2274-2284 (May 1, 1996).

Gloge, D., et al., "Weakly Guiding Fibers", Applied Optics, vol. 10, No. 10, 2252-2258, Oct. 1971.

Lin, Binhua, et al., "Static and dynamic evanscent wave light scattering studies of diblock copolymers adsorbed at the air/water interface", J. Chem. Phys., 99(10), 8308-8324, Nov. 1993.

Langley, Kenneth H., et al., "Light Scattering and Other Optical Methods", Experimental Methods in the Physical Sciences, vol. 35, 263-300 (1999).

Yang, Xin, et al., "Optical-fiber sensor for determining water content in organic solvnets", Sensors and Actuators B, 3703, 1-5 (2001).

Bonin, Hugues W., et al., "Design of a Neutron Gauge for the Detection and Measurement of Water Ingression in Flat Roofs", Nuclear Technology, vol. 95, Sep. 1991.

Al-Qadi, Imad, et al., "Using Microwave Measurements to Detect Moisture in Asphaltic Concrete", Journal of Testing and Evaluation, JTEVA, vol. 20, No. 1, pp. 43-50, Jan. 1992.

Khijwania, et al., "Fiber optic evanescent field absorption sensor: Effect of fiber parameters and geometry of the probe"; Optical and Quantum Electronics, 31:625-636, 1999.

Jindal, et al., "High dynamic range fiber optic relative humidity sensor", Optical Engineering, vol. 41(5), pp. 1093-1096, May 2002.

* cited by examiner

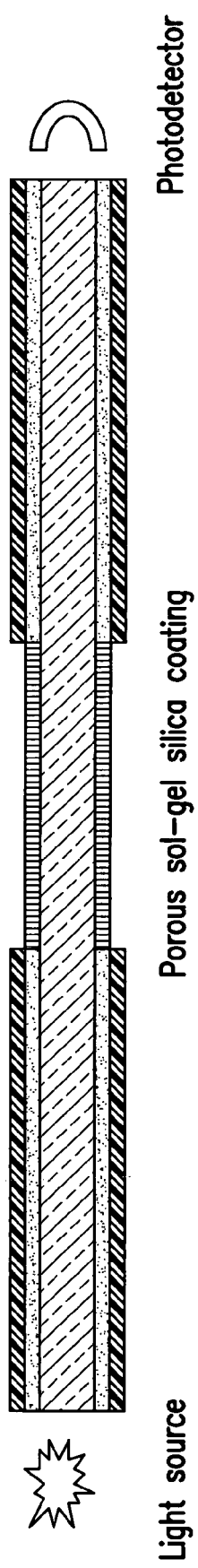
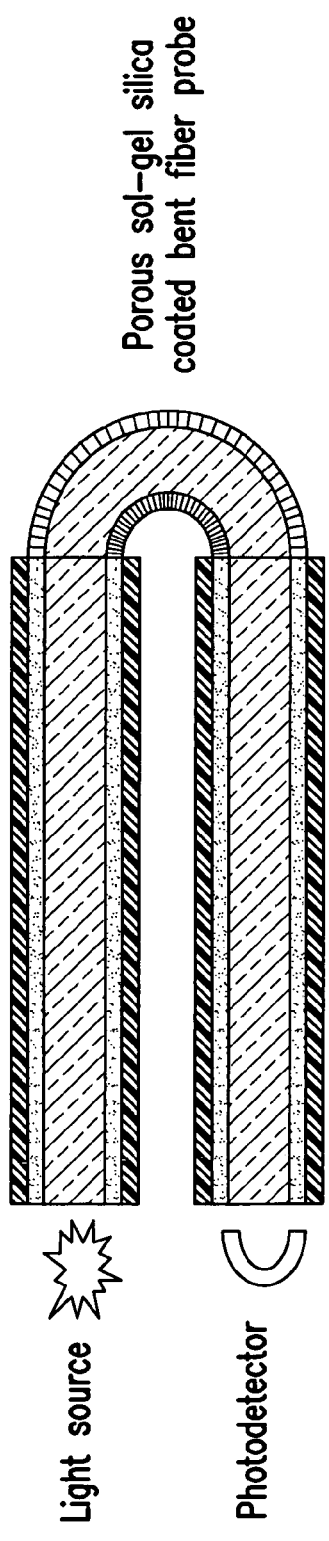
FIG.1A
FIG.1B

Light intensity guided through a bent optical fiber with and without sol-gel silica coating Experimental set-up for testing the optical fiber moisture sensor dB response of a sol-gel silica coated bent fiber probe to air gas of different humidity against wavelength Calibration curve of a sol-gel silica coated bent fiber probe for moisture sensing Time response of a sol-gel silica coated bent fiber probe to moisture change Comparison of response time of a sol-gel silica coated bent fiber moisture sensor with a capacitance based commercial sensor Calibration curves of a sol-gel silica coated bent fiber sensor on different dates (The probe was soaked in water in between each test)

Long-term soil moisture monitoring using a sol-gel silica coated bent fiber sensor (The coated bent fiber probe was buried in soil sample without any package protection)

Laboratory set-up for testing the sensor of this invention for monitoring moisture inside a concrete block Preliminary test result of optical fiber sensor for monitoring moisture in concrete block

MOISTURE SENSOR BASED ON EVANESCENT WAVE LIGHT SCATTERING BY POROUS SOL-GEL SILICA COATING

This invention was made with Government support under DE-FC26-98FT40395 awarded by the U.S. Department of Energy. The Government may have certain rights in the invention.

BACKGROUND OF THE INVENTION

1. Field of the Invention

The present invention relates generally to moisture sensors, and more particularly to optical fiber moisture sensors and methods for manufacturing the same.

2. Related Art

The monitoring and controlling of gas phase water content is required in many fields. Such fields include daily air quality management, weather broadcasting, agricultural activity, industrial process control in tobacco production, food processing, oil refinement, metal processing, high purity gas preparation, semiconductor production, etc.

In such varying fields, different applications require different sensors to monitor water concentration in a specific gas environment. For example, in a tobacco production line, a humid air environment (i.e., relative humidity is equal to 60% to 80%) is required in order to preserve the quality of the tobacco leaves. In such an application, a sensor with sensitivity for detecting water content of x % is appropriate and sufficient. However, in a semiconductor production line, water content in the gas stream needs to be controlled in the sub-part-per-billion level. Such an application requires a technique with very high sensitivity to monitor water content in the gas phase. An example of a sensor implementing such a technique (e.g., the Cavity Ring-Down Spectroscopy (CRDS) technique) is available from Tiger Optics, LLC of Warrington, Pa.

Present techniques for monitoring moisture include those that are based on the change of some electric property as detected by a specially-designed resistor or capacitor as described in U.S. Pat. No. 5,040,090 issued to Birkle et al.; and Raj et al., "Sensors and Actuators," B: Chemical, B81(2–3), 229–236 (2002). Sensors based on these techniques are used in such applications as air quality management, food process control, soil analysis, etc. Because metal electrodes are used in the fabrication of such electric property based sensors, however, they normally have problems in applications involving corrosive environments where a high temperature gas stream, a gas stream of high humidity or a gas stream containing acidic species (e.g., $SO_2$, NOx, HCl) is present. Further, these electric property based sensors are also susceptible to electromagnetic noise, which limits the applications in which they can be used.

An alternative to electric property based sensors is optical fiber moisture sensors based on end-point membrane light absorption, evanescent wave optical absorption, or evanescent wave excited fluorescence. These optical fiber sensors have several advantages over electric property based moisture sensors. These advantages include smaller size, easier and cheaper fabrication, lower operating costs, and immunity to electromagnetic noise. In addition, distributed optical fiber sensors can be made in a single fiber to sense moisture in different locations at the same time.

U.S. Pat. No. 4,634,856 issued to Kirkham describes a light absorption based optical fiber sensor where a reflective target is attached on one end of an optical fiber. The reflectance of the target depends on the content of moisture in gas phase surrounding the target. Kirkham also describes a moisture sensor based on the change of reflective index of the clad of an optical fiber.

U.S. Pat. No. 5,319,975 issued to Pederson describes a fluorescence based optical fiber sensor for moisture sensing. The transducer of this sensor is a reagent-trapped membrane that is attached to one end of an optical fiber. A monochromatic light beam, which is obtained by passing light from a high intensive lamp through a monochromator, is fed into the second end of the fiber to excite the fluorescence of the reagent trapped in the membrane. A second optical fiber is used to collect the fluorescence from the membrane. When the membrane is exposed to humid air the fluorescence is quenched. This sensor is described as being able to detect moisture to less than 10% relative humidity.

U.S. Pat. No. 4,894,532 issued to Peterson et al. describes a plasma polymerization method to coat polymer from a gas mixture of hexamethyldisiloxane and ammonia on the surface of an optical fiber core. While the characteristics of the coated polymer are not described in Peterson et al., the polymer is described as absorbing light guided through the optical fiber on which the polymer was coated. The polymer coating process is complex and time consuming. Peterson et al. describes a process where eleven hours of plasma discharge is required to coat the polymer onto the surface of a fiber core.

Optical fiber sensors based on indicators trapped in polymer coatings have also been reported. See, e.g., Hypszer et al., SPIE, vol. 3054, 145–150 (1997); and Jindal et al., Optical Engineering, vol. 41, 1093–1096 (2002). $CoCl_2$ is the most frequently used indicator in these sensors. $CoCl_2$ can absorb light with a large peak-absorption at around 690 nm and a minor peak-absorption at around 550 nm. This compound can form a complex with water molecules when exposed to humid air. The complex absorbs light with peak absorption at around 550 nm. $CoCl_2$ is usually doped in a polymer, such as polyvinylalcohol (PVA), polymethylmethacrylate (PMMA), gelatin, polyvinylpyrrolidone, etc.

To construct the transducer of an optical fiber sensor the $CoCl_2$ doped polymer is coated on top of an optical fiber core. A (He—Ne) laser is usually used as a light source to probe the absorption signal. As observed in Hypszer et al., a $CoCl_2$ doped optical fiber moisture sensor usually cannot obtain a linear calibration for a wide humidity range. It is the concentration of $CoCl_2$ complex with water, $Co[H_2O]_6Cl_2$, which has linear relationship with water content in gas phase. However, the absorption signal of $Co[H_2O]_6Cl_2$ cannot be used in these sensors because $CoCl_2$ also absorbs light at the peak absorption wavelength (i.e., 550 nm) of the complex. These sensors usually monitor the absorption signal of $CoCl_2$ at 630 nm. This signal, however, is not proportional to water molecule concentration in gas phase.

Optical fiber sensors with organic polymer as a coating material are also limited in the applications for which they can be utilized due to the stability of organic polymer when exposed to severe environment (e.g., high temperature, corrosive gas, intensive ultraviolet light radiation, etc.).

Therefore, given the above, what is needed is an optical fiber moisture sensor that overcomes the above-described limitations and is capable of being used in varying applications.

SUMMARY OF THE INVENTION

The present invention meets the above identified needs by providing a porous sol-gel silica polymer coated on an optical fiber core that forms the transducer of an optical fiber moisture sensor. In constructing the sensor, the sol-gel silica coated optical fiber is further connected to a simple light source, such as a battery-powered light emitting diode (LED), and a photodetector.

In an embodiment, the sol-gel silica coating on the optical fiber core consists of nanometer ($10^{-9}$) silica particles, which are connected to each other to form a porous structure. When a light beam is guided through the sol-gel silica coated optical fiber, the evanescent wave which forms in the cladding layer of the fiber is scattered out of the fiber by the porous sol-gel silica coating (evanescent wave light scattering or "EWLS"). This EWLS attenuates the light intensity guided through the optical fiber. However, the surface of the sol-gel silica particles is highly hydrophilic and has strong tendency to absorb water molecules from its surrounding environment. The absorbed water molecules form a thin layer of liquid water on the inner surface of the pores of the porous sol-gel silica and enhance the light scattering effect, from which a sensing signal can be obtained.

Sol-gel silica is a very stable material which results in a sensor based on a such a coating being operable in severe environments where a high temperature gas stream, outdoor air, soil gas and gas stream containing corrosive acidic components are present. A sol-gel silica coating based moisture sensor also exhibits fast response times. This makes such a sensor useful in certain fast event control applications, such as leakage monitoring in high purity gas preparation, semiconductor production lines and the like.

An advantage of the present invention is that it provides techniques for making optical fiber moisture sensors that can be used to sense moisture present in gas phase in a wide range of concentrations.

Another advantage of the present invention is that it provides an optical fiber sensor that can be used in various applications, including to sense: moisture content in indoor/outdoor air, moisture in soil, moisture in concrete, and water content in a high temperature gas stream.

Another advantage of the present invention is that it provides a method for coating the core of an optical fiber with a porous sol-gel silica, treating the surface of the optical fiber core before applying the sol-gel silica coating, and coating the optical fiber core with a silicone rubber layer on the top of the sol-gel silica coating.

Yet another advantage of the present invention is that it provides a method for using the light scattering phenomenon which occurs in the sol-gel silica coating for sensing moisture.

Further features and advantages of the present invention as well as the structure and operation of various embodiments of the present invention are described in detail below with reference to the accompanying drawings.

BRIEF DESCRIPTION OF THE FIGURES

The features and advantages of the present invention will become more apparent from the detailed description set forth below when taken in conjunction with the drawings.

FIG. 1A is a block diagram illustrating an optical fiber moisture sensor using a straight fiber core according to an embodiment of the present invention.

FIG. 1B is a block diagram illustrating an optical fiber moisture sensor using a bent fiber core according to an embodiment of the present invention.

DETAILED DESCRIPTION

Figure 2:
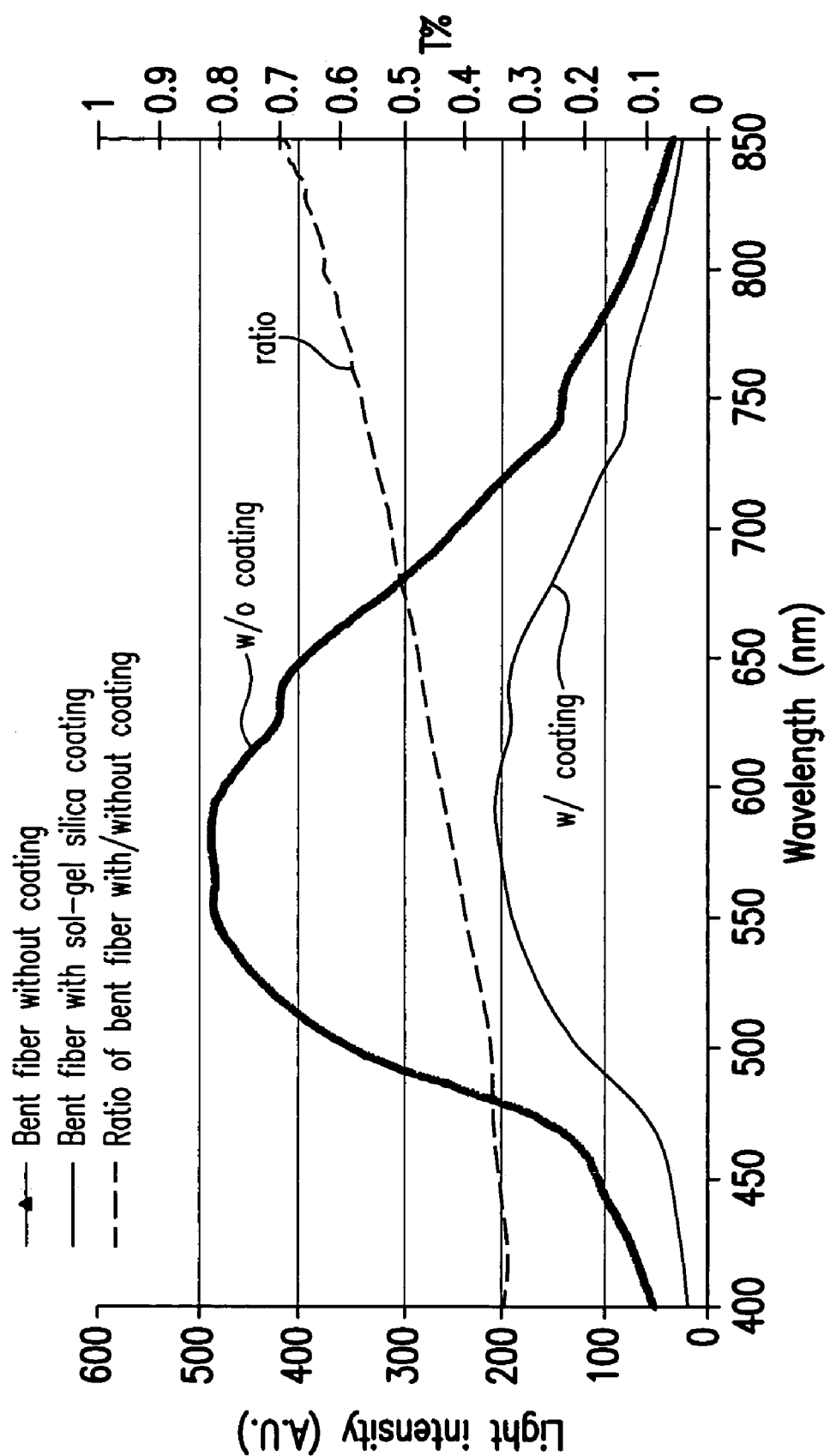
FIG. 2 is a graph plotting and comparing the wavelength dependent of light intensity guided through an untreated and treated bent fiber according to an embodiment of the present invention.

The present invention is directed to a porous sol-gel silica polymer coated on an optical fiber core that forms the transducer of an optical fiber moisture sensor. That is, in an embodiment, a moisture sensor based on evanescent wave light scattering by porous sol-gel silica coating is provided by the present invention.

I. Sensor Fabrication

In an embodiment, the transducer of an optical fiber moisture sensor of the present invention is an optical fiber coated with porous sol-gel silica. The porous sol-gel silica is coated on the top of an optical fiber, a portion of which the original jacket and cladding has first been removed (interchangeably referred to herein as an "optical fiber core" or "fiber core"). In alternate embodiments, the coated optical fiber core can be straight or be bent in a "U" shape. The optical fiber moisture sensors using a straight fiber core and a bent fiber core are shown in FIG. 1A and FIG. 1B, respectively.

The principle of moisture sensing of the sensors shown in FIGS. 1 A–B are the same. However, a bent fiber probe usually has higher sensitivity compared with a straight fiber probe. This is because there is more light leaking out of the fiber core to interact with the sensing material in the cladding layer in the bent part of the fiber as observed in Khijwania et al., Optical and Quantum Electronics, vol. 31, 635–636 (1999). Therefore the "U" bent fiber probe embodiment is used to describe the present invention in greater detail. This is for convenience only and is not intended to limit the application of the present invention. In fact, after reading the following description, it will be apparent to one skilled in the relevant art(s) how to implement the following invention in alternative embodiments (e.g., utilizing a straight optical fiber core or other configurations such as an "S" shape, serpentine, coil, angular, etc.).

In an embodiment of the present invention, the bent probe of FIG. 1B is made by the following procedure:

First, two ends of a commercially-available optical fiber are polished. A small part (e.g., 0.5 to 2 cm) in the center of the optical fiber is inserted into a flame to burn off the jacket and cladding of such small part. The resulting optical fiber core portion of the fiber is then further bent into a "U" shape while in the flame.

After cooling to room temperature, the bent part is soaked in a solution to wash off any organic material possibly sticking on the surface of the bent part of the fiber. In a preferred embodiment, this is accomplished by soaking the bent part in a hot solution of $K_2Cr_2O_7/H_2SO_4$ for at least 30 minutes. The bent part is then taken out of the solution and rinsed with de-ionized (DI) water.

Next, the bent part of the fiber is further soaked in another solution to activate its surface hydroxyl groups. In a preferred embodiment, this is accomplished by soaking the bent part of the fiber in a solution which is at least 2 M NaOH for at least 12 hours to activate its surface hydroxyl groups. After rinsing the bent probe with DI water, it is coated with sol-gel silica, by for example, dipping it into a silica sol solution at least six times. The coated probe is then kept in a refrigerator for at least 12 hours before use.

In an embodiment, the sol-gel silica coating solution is made by hydrolysis of a liquid ester of a silicic acid in the presence of a trace catalyst. Examples of a liquid ester of a silicic acid include tetramethyl orthosilicate and tetraethyl orthosilicate. In an embodiment, a suitable trace catalyst is ammonia or a mineral acid catalyst such as hydrochloric acid as described in Tao et al., Optics Letters, vol. 27, 1382–1384 (2002). The resulting liquid sol solution of silicic acid and organic alcohol is stored in a refrigerator before use. The silicic acid molecules in the liquid react slowly with each other to form a polymer during the storage. In a preferred embodiment, the coating of the probe is applied within twelve hours after the hydrolysis.

Examples of silicate esters include tetramethyl orthosilicate and tetraethyl orthosilicate.

In a preferred embodiment, a moisture sensor of the present invention consists of a light source, a bent optical fiber probe coated with a sol-gel silica (prepared as described above) and a photodetector. A typical sensor of the present invention is shown in FIG. 1B, in which a near infrared light emitting diode (NIR LED) is used as a light source and a photodiode (PD) is used as a photodetector.

II. Evanescent Wave and EWLS by Sol-Gel Silica Coated on an Optical Fiber Core

When a light beam is guided through an optical fiber, a standing wave is formed in the cladding layer of each point of total internal reflection. This standing wave distributes a small part of the light guided through the fiber into the cladding layer as described in Messica et al., Applied Optics, vol. 35, 2274–84 (1998). The part of the light that leaks into the cladding layer is referred to as an "evanescent tail." The intensity of the evanescent tail depends on fiber diameter, reflective index of the fiber core and cladding, and the wavelength of the light guided through the fiber as discussed in D. Gloge, Appl. Optics., 10 (10), 2252–58 (1971). The intensity of the evanescent tail also depends on the configuration of the fiber. When an optical fiber is bent, there is more light distributed into the cladding layer in the bent part as observed in Khijwania et al.

In an optical fiber made for communications purposes, the polymer layer used for cladding the fiber is made uniform and the microstructure is eliminated. Therefore, light scattering loss in this polymer cladding is negligible for the light used for communications purposes. However, in constructing an optical fiber moisture sensor, the cladding layer of an optical fiber made for communications purposes is removed and a new polymer layer is coated on the surface of the fiber core. If the new coating has an appropriate microstructure, a light scattering phenomenon in the coating layer can be observed. This evanescent wave light scattering (EWLS) phenomenon has been used in studying polymer structure as discussed in B. Lin et al., Journal of Chemical Physics, vol. 99, 8308–24 (1993).

Sol-gel silica is a porous material. It is formed through the interconnection of nanometer silica particles. When light leaks into a sol-gel silica coating on the top of an optical fiber core, EWLS occurs due to the porous structure.

The scattering attenuation caused by the sol-gel silica coating against the wavelength of light guided through the bent fiber probe was tested by the inventors of the present invention. Two bent optical fibers were made by following the procedure described above. One of the bent fibers was further coated with sol-gel silica as described above. In the test, the bent fiber without sol-gel silica coating was connected to a tungsten lamp and a fiber optic spectrometer. The light intensity versus wavelength guided through the bent fiber to the spectrometer was recorded. The sol-gel silica coated bent probe was then connected to the light source and the spectrometer, and then the light intensity versus wavelength was also recorded.

FIG. 2 shows the recorded light intensity of the two probes. The intensity of light guided through the sol-gel silica coated bent probe is much lower than that of the bent probe without coating through the entire recorded wavelength range. FIG. 2 also shows the ratio of the light intensity versus wavelength guided through these two bent probes. As one skilled in the relevant art(s) will appreciate, the light loss due to EWLS in the sol-gel coated bent probe is wavelength dependent in the tested wavelength range.

The mechanism of light scattering in the porous sol-gel silica coating is complex. In the porous material, there is an abrupt change of refractive index at the pore walls. When a light beam is guiding through such a porous material, the light is diffused at the wall of the pores. This scatters the light out of the porous material. Langley et al., Experimental Methods in the Physical Sciences, vol. 35, 263–300, (1999), analyzed the light scattering phenomenon observed in such porous material by using diffusing-wave spectroscopy. In a simplified backscattering model, Langley et al. expressed the scattered light intensity as:

$$I_E = \exp(-k\gamma\lambda)$$

In the above equation, $\gamma$ is proportional to the reciprocal of the mean free path length of light propagation in the porous material, $\lambda$ is the wavelength of light, k is a constant. This equation indicates that the scattered light intensity is proportional to the negative exponent of wavelength. This explains the test results of wavelength dependence of transmittance of the sol-gel coated fiber probe shown in FIG. 2.

III. Sol-Gel Silica Coating EWLS for Moisture Sensing

The pore surface of porous sol-gel silica is hydrophilic and has a strong tendency to absorb water molecules from gas phase through hydrogen bond formation. The absorbed water molecules form a layer of liquid water on the surface of the pore walls. Therefore, there are three phases (solid sol-gel silica, liquid water and air gas) in such a porous material. When a light beam is guiding through such a porous material, the light is diffused first in the solid-liquid interface and again in the liquid-gas interface. With a higher humidity in the gas environment around such a material, more water molecules are absorbed onto the inner surface of the pores and a thicker liquid film is formed on the inner surface of the pores. This thicker film increases the free path length of light propagation in the liquid phase and thus enhances the scattering of light in the liquid-gas interface (Langley et al.). Therefore, the water absorbing property of porous sol-gel silica can be used to sense the concentration of water molecules in gas phase.

Figure 3:
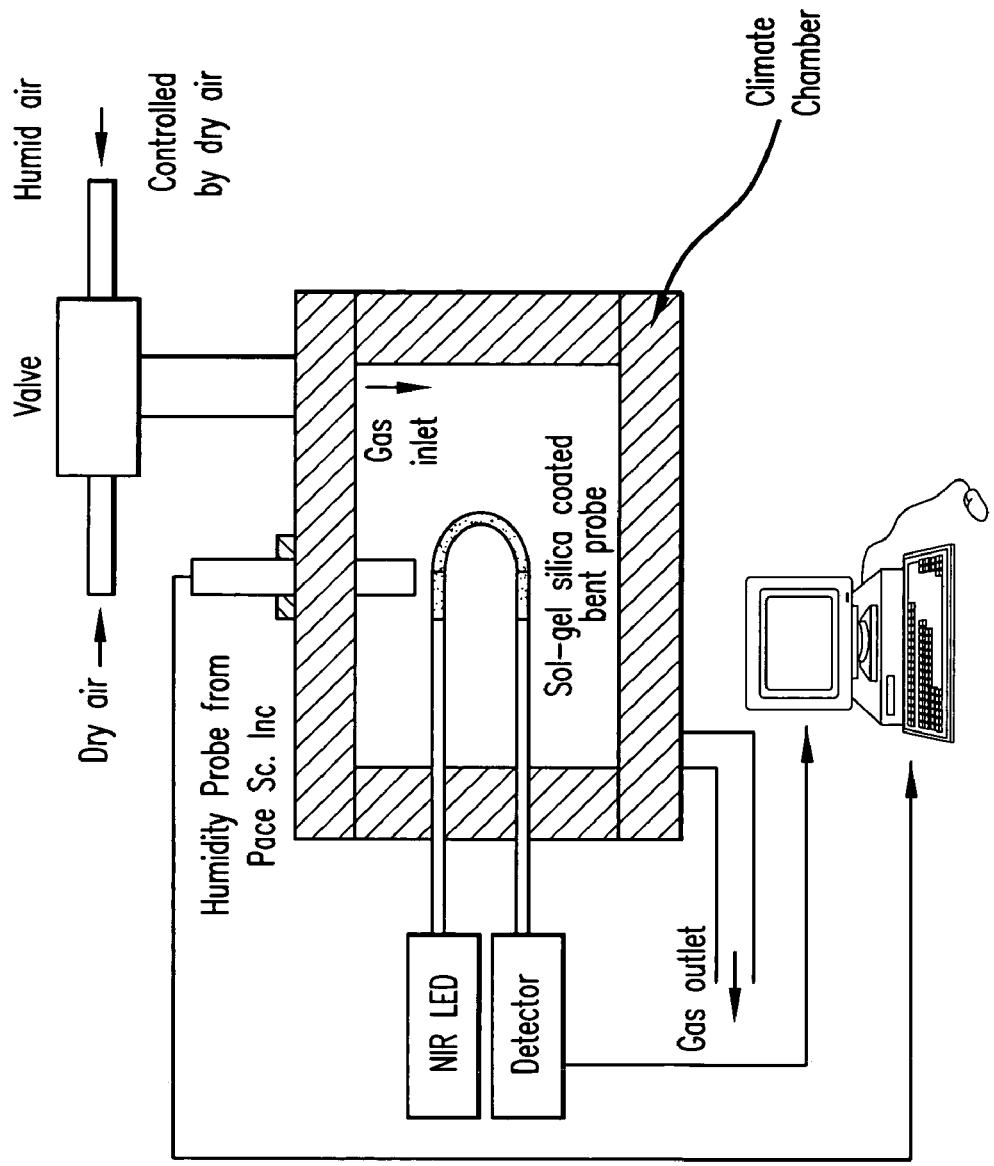
FIG. 3 is a block diagram illustrating an experimental setup for testing an optical fiber sensor according to an embodiment of the present invention.

The light-guiding efficiency of the sol-gel silica coated bent probe used in the previous experiment (FIG. 2) in air gas of different moisture content was tested. The bent part of the probe was set inside a climate chamber (as shown in FIG. 3) together with a capacitance-based moisture sensor. The two ends of the probe were connected to the tungsten lamp and the fiber optic spectrometer as done in the previous experiment (of FIG. 2). Two gas streams, a dry air stream and a humid air stream, were combined in a "Y" connector and the resulting mixed gas was allowed to flow into the chamber. The moisture content of the air inside the chamber, expressed as relative humidity (RH %), was controlled by adjusting the flow rate of the dry air and the humid air streams. In the test, the RH % of the mixed air gas in the chamber was adjusted to different values and the light intensity guided through the probe was recorded in the wavelength range of 400 nm to 850 mm.

Figure 4:
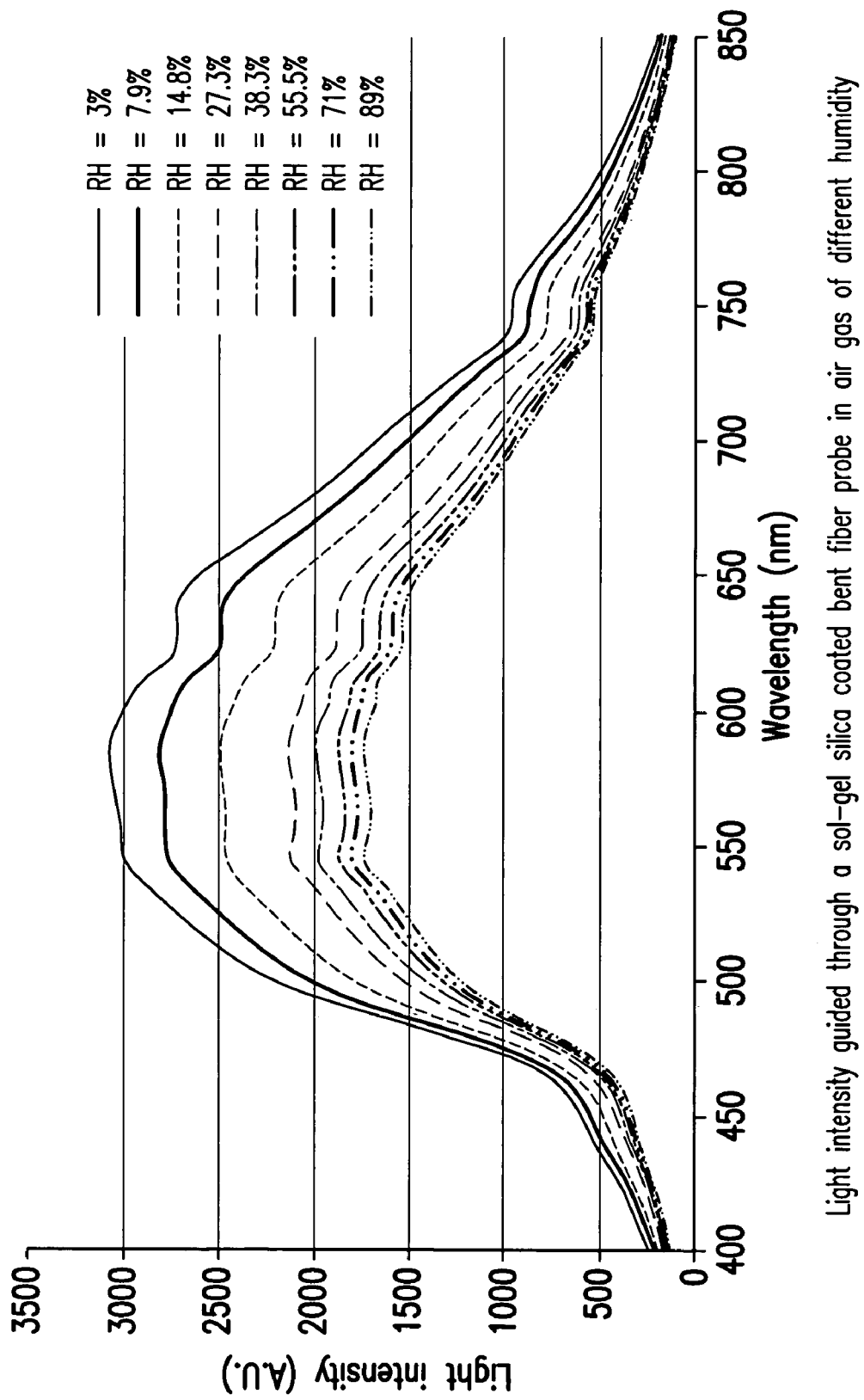
FIGS. 4–8 are graphs plotting various results of the experimental setup shown in FIG. 3 for testing the optical fiber sensor according to an embodiment of the present invention.

Results of the above-described test are shown in FIG. 4. With the increase of RH %, the intensity of light guided through the probe decreases in the whole recorded wavelength range. Taking the transmitted light intensity of 3% relative humidity as the maximum guided intensity, the attenuation of light intensity expressed in decibels (dB) is calculated as follows:

$$dB = 10 * \log(I_{3\% RH}/I)$$

In the above equation, $I_{3\% RH}$ is the intensity at 3% RH and I is the intensity of light measured at the output end of the probe which can be measured in any arbitrary unit (shown as "AU" in FIG. 4). (As will be appreciated by one skilled in the relevant art(s), because 0% RH is not achievable in a lab environment, 3% RH—the lowest humidity achievable in a typical lab environment using a desiccant—as the comparing point.) The relationship of dB versus wavelength at different humidity values is plotted in FIG. 5, which clearly illustrates that the sensing signal in dB is independent of wavelength above 650 nm. A calibration curve was obtained by plotting the sensing signal in dB at 800 nm against the relative humidity of the air gas inside the chamber (FIG. 6). The relationship between the light intensity and the relative humidity for the specific probe follows the equation:

$$dB = -n \log(RH) + k$$

Where, in the above equation, k is a constant.

Figure 5:
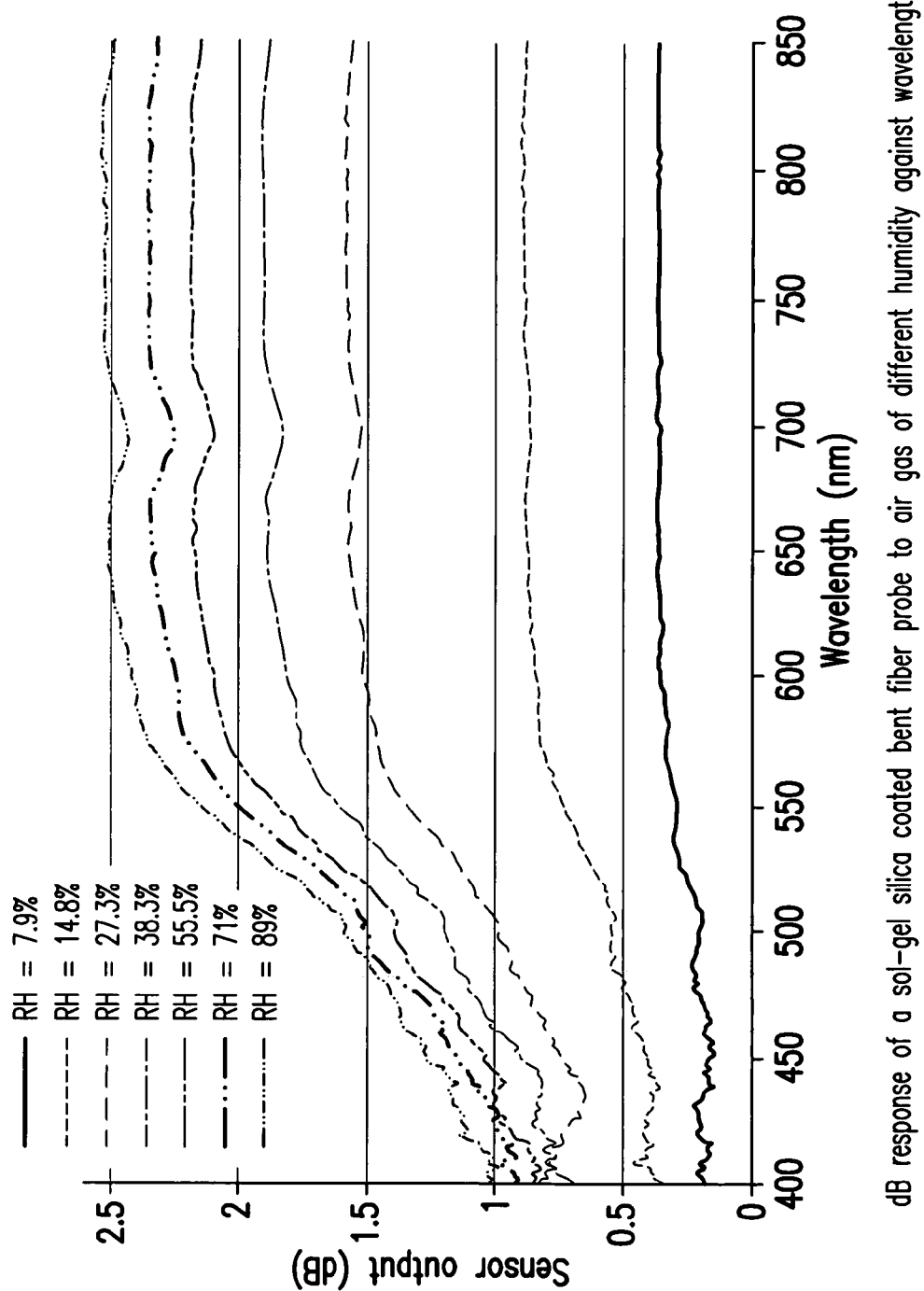
Figure 6:
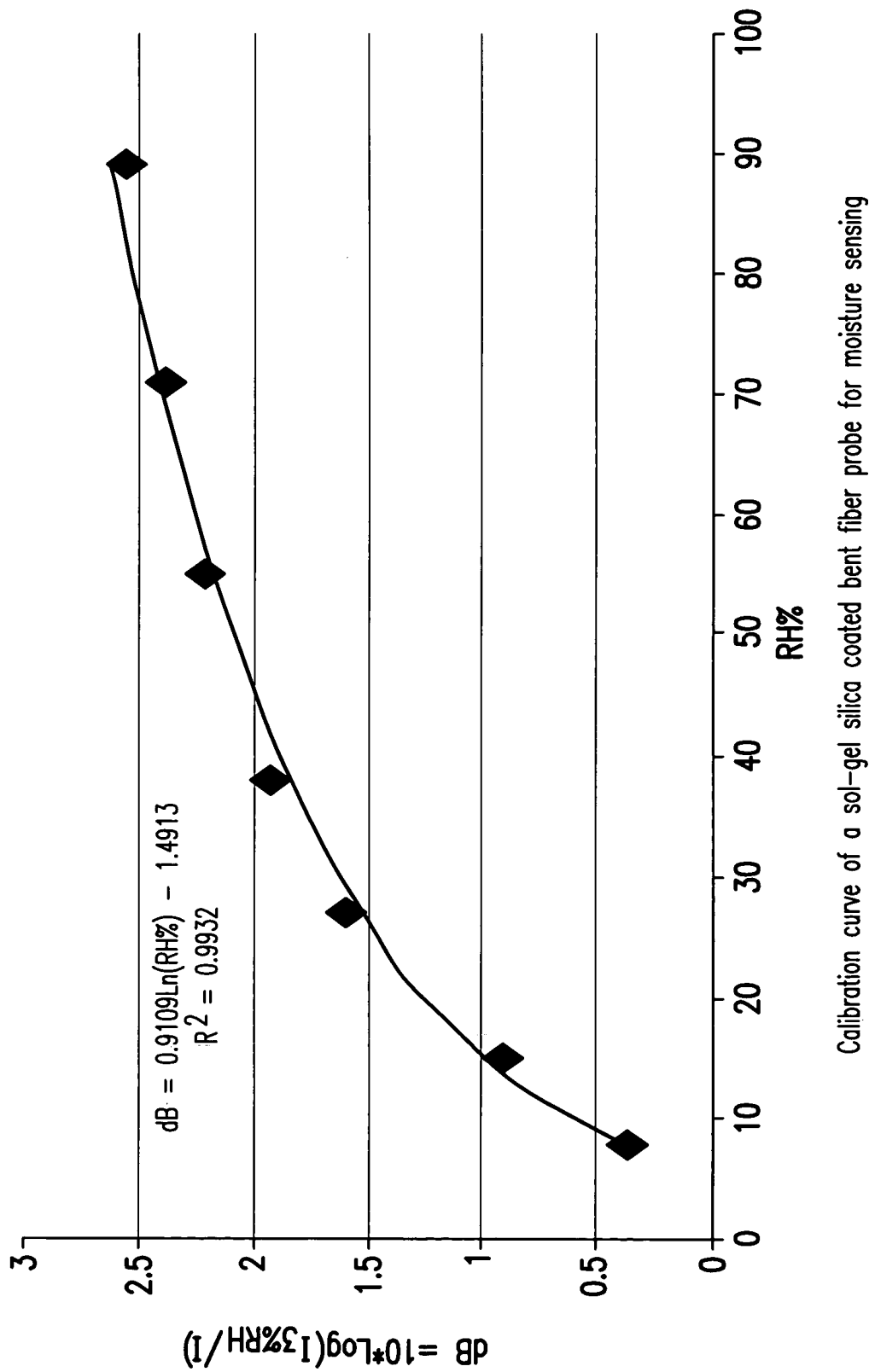

As shown in FIG. 5, the calibration curve plotted using the dB signal at other wavelengths above 650 nm should also follow the same equation. Therefore, the wavelength and bandwidth of the light source are not specifically required as far as the light source can emit intensive enough light at wavelengths longer than 650 nm. This makes it possible to use a very simple and cheap light source in designing sensors according to the present invention.

IV. EXAMPLES

Example 1

Moisture Sensor for Sensing Relative Humidity (RH %) in Air Gas

Moisture content in air gas is an important factor which affects the quality of human life as well as the quality of many industrial products. Moisture sensors based on electric capacitance or resistance between two specially designed electrodes have been developed and commercialized (Birkle et al. and Raj et al.). However, fiber optic moisture sensors based on light absorption and fluorescence have been the recent focus of research.

A sensor of the present invention for sensing moisture in air gas was fabricated by connecting a sol-gel silica coated bent fiber probe to a near infrared light emitting diode (NIR LED) and a photodiode detector. The formed sensor structure is shown in FIG. 1B. The light from the NIR LED was directly fed into the bent fiber probe without any light-focusing element. The response of the sensor to humidity change was tested by using the climate chamber as described above (and shown in FIG. 3).

Figure 7:
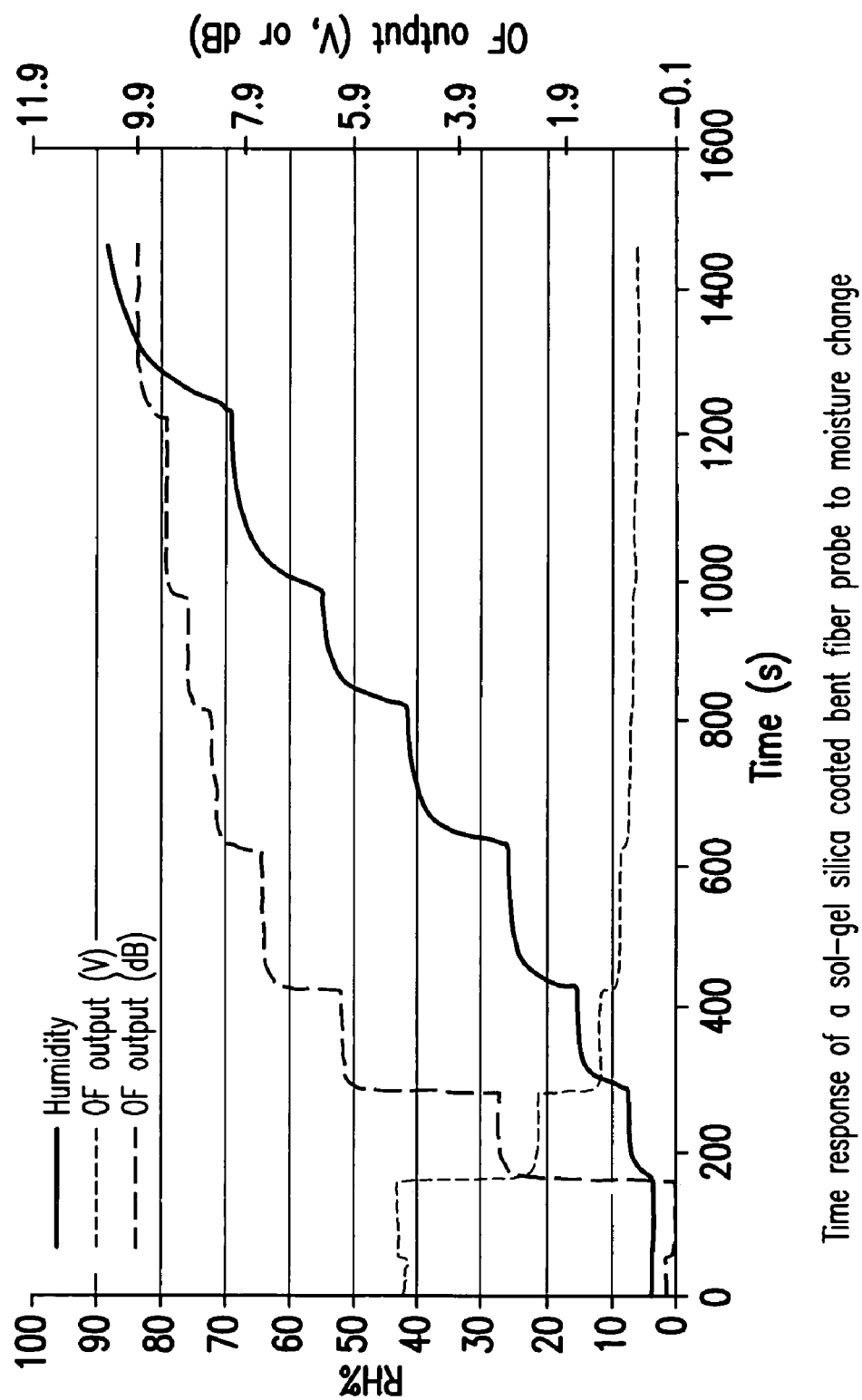
Figure 8:
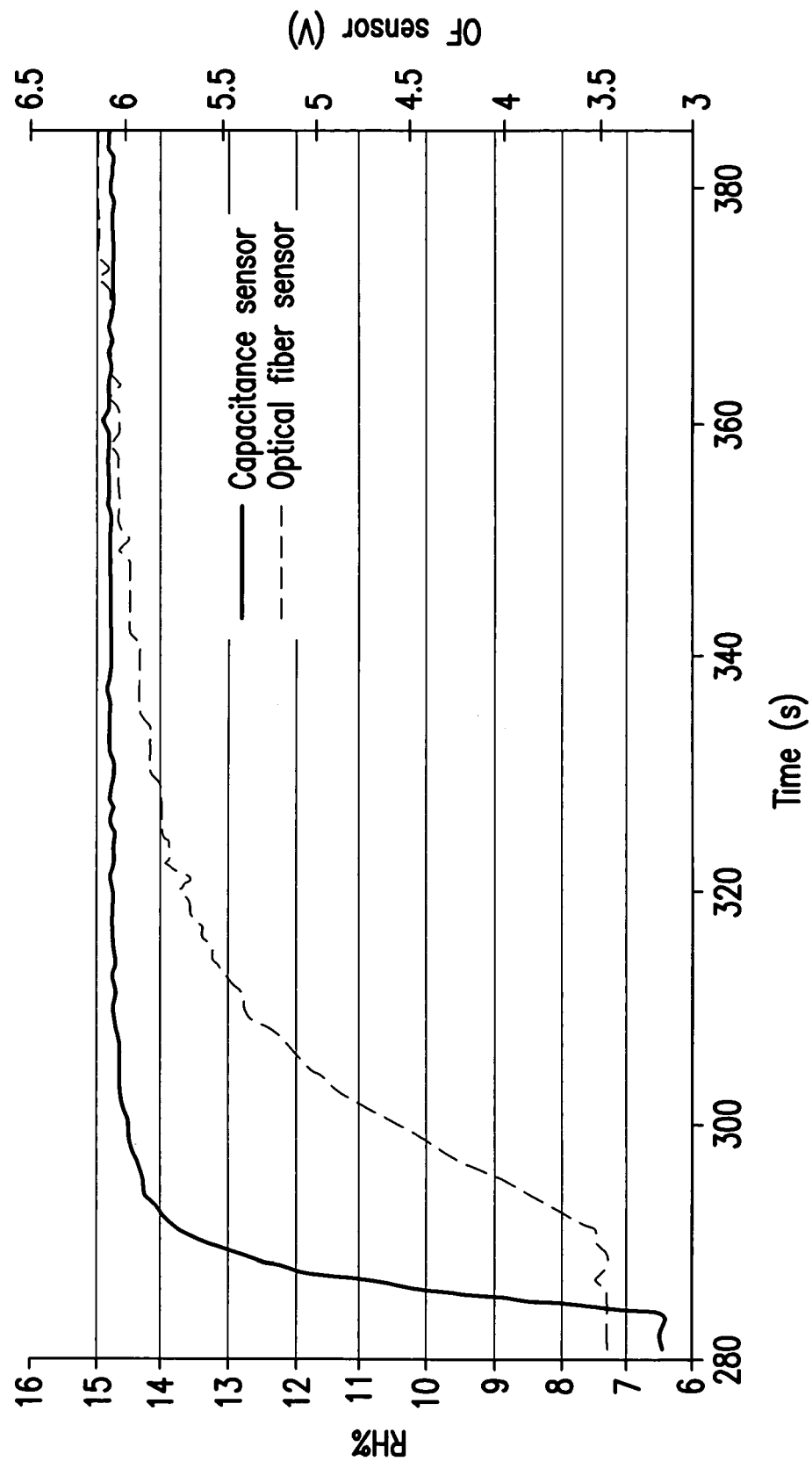

The recorded response time of the sensor to humidity change is shown in FIG. 7. With the increase of relative humidity in air gas, the bent probe scatters more light out of the fiber and light intensity detected in the output end (i.e., photo diode detector) decreases. The absorption of a water molecule on the surface of a sol-gel silica particle is a reversible process. Therefore, when the humidity in the climate chamber decreases the light intensity detected in the output end increases. The second feature of the sensor of the present invention, as shown in FIG. 8, is that its response to humidity change is almost instant when compared to conventional sensors based on electric capacitance.

Two factors are thought to contribute to the fast response of the sensor of the present invention. First, the surface of the interconnected sol-gel silica particles is highly hydrophilic. The particles have strong tendency to absorb water molecules. Second, the absorption only occurs in the surface of the particles. In addition, the thickness of the sol-gel silica coating is in the micrometer level. Water molecules can easily diffuse into the porous coating layer. Therefore, the absorption is very fast. The fast response of the sensor of the present invention is significant when compared with some polymer coating based sensors. For example, the response time of a $CoCl_2$/PVA coating based sensor in low humidity range is longer than ten minutes as shown in Jindal et al. The fast response feature of the sensor of the present invention makes it useful in many industrial process control applications. For example, it can be used for leakage detection in high purity gas preparation.

Example 2

Soil Moisture Sensing

Soil moisture information is valuable to a wide range of government agencies and private companies concerned with the weather, climate, soil erosion, reservoir management, waste tank management, geotechnical engineering, farmland irrigation, underground water resources exploration, etc. In almost all of these applications, continuous monitoring of soil moisture is required. Soil moisture sensors based on the detection of electric properties, such as dielectric constant or resistance, have been developed and commercialized. These sensors, however, suffer from the corrosive environment of soil. That is, the electrodes of these conventional sensors gradually corrode in the soil, thus limiting their life-span.

Fiber optic moisture sensors based on polymer coatings with a light absorption indicator or fluorescence reagent have been developed (Yang, Sensors and Actuators B, vol. 3703, 1–5 (2001); Hypszer et al.; and Jindal et al.). For most of the reported optical fiber sensors, however, the stability of the reagent in the soil environment is an obstacle for wide acceptance of their application for soil moisture monitoring. In the gas phase inside soil, there are many chemical compounds such as ammonia, organic amine, hydrogen sulfide, etc. Some of these compounds can react irreversibly with the reagent doped in the polymer and deactivate the sensor permanently. In addition, some polymers or reagents can dissolve in water when the sensor is soaked in water for a long time, which happens in soil. Moreover, there are typically many dissolved chemicals in the water when a soil sample is soaked in water. These chemicals can also irreversibly react with the reagent or the polymer of the optical fiber sensors and deactivate the sensors.

Figure 9:
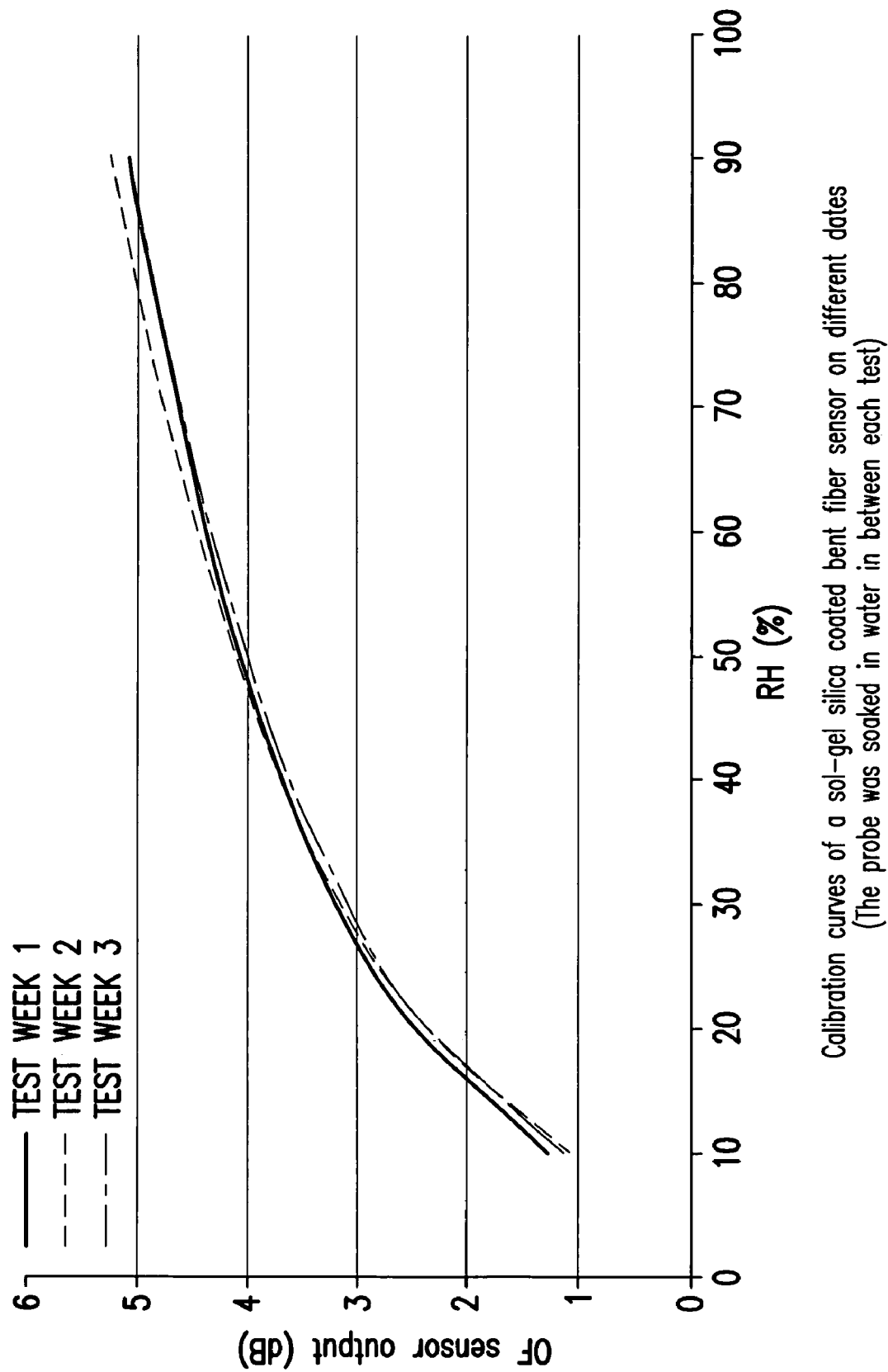
FIGS. 9–10 are graphs plotting various results of experiments designed to test the capability of the optical fiber sensor according to an embodiment of the present invention for use in long-term soil monitoring applications.

In an embodiment, the transducer of the optical fiber sensor of the present invention is a thin layer of sol-gel silica coating. In such an embodiment, there is no other reagent used in this sensor. The chemical composition of the coating is silicon dioxide which is a very stable material and is insoluble in water. Therefore, the sensor can still function properly after being soaked in water for extended periods of time. FIG. 9 shows the response of a sol-gel silica coated bent probe sensor to moisture change for three separate tests in which the probe was soaked in water for one week in between each such tests. It can be concluded from this series of tests that there is no observable change in the sensor's response to moisture after long periods of soaking the probe in water.

There are many water-soluble compounds and colloid particles in soil water. These compounds and colloid particles can be absorbed on the surface of the sol-gel silica particles and change the surface property of the sol-gel silica particles.

Therefore, a protective coating, which is permeable to water vapor but blocks out liquid water, is essential to isolate the sol-gel silica coating from soil water. In an embodiment, silicone rubber is chosen as the protective coating material. One example of a silicone coating method includes dipping the sol-gel coated fiber in a silicone rubber coating mixture and drying the optical fiber for at least 24 hours. In a related aspect, the mixture includes a silicone elastomer and a curing agent, where the mixture is diluted in toluene. Silicone rubber is highly permeable to water vapor and can block out liquid water. After applying a thin layer of silicone rubber protective coating on the top of the sol-gel silica coating, the resulting sensor can be used for long-term soil moisture monitoring. Another example includes preparing a mixture comprising a silicone elastomer and a curing agent, where such a mixture is diluted with toluene.

Figure 10:
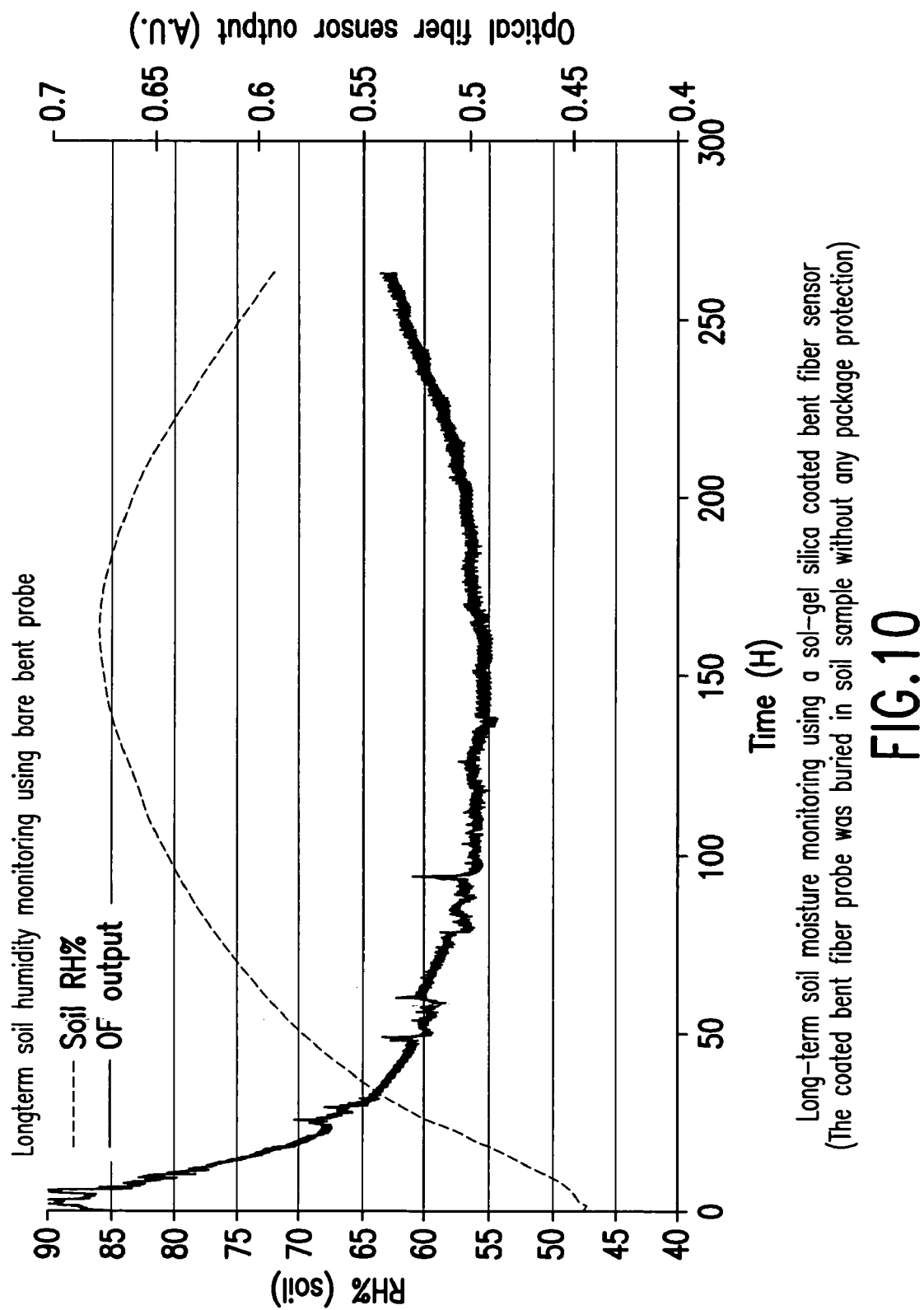

A sensor of the present invention having the same structure as that used for air humidity sensing as described above, but also having a silicone rubber protective coating as described above, was fabricated. The resulting sensor was buried together with a capacitance based moisture sensor into a dry soil sample in a flowerpot. The sensing signals of both the sensors were monitored. Water was applied to the soil sample to slowly change the moisture content of the sample. Test results are shown in FIG. 10. In this long-term test, water content of the soil was very high during some of the time periods. However, the high water content did not affect the sensor of the present invention. Therefore, this test result verified the capability of the sensor of the present invention to be used for long-term soil moisture monitoring applications.

As will be appreciated by those skilled in the relevant art(s) after reading the description herein, in alternate embodiments, other permeable protective coatings than silicone rubber can be applied on the top of the sol-gel silica coating (e.g., permeable polymers, permeable plastics, permeable thermoplastics, permeable polyurethanes, permeable gels and the like).

Example 3

Concrete Moisture Sensing

Concrete is the most widely used construction material in the world and is used in buildings, houses, bridges, roads, airport runways, etc. The strength and stability of the utilized concrete is thus critical to the life-span of the resulting constructed structure. Concrete is a living material and its durability and any structural ageing is governed by moisture content.

Water is at the heart of most of the physical and chemical causes underlying the deterioration of concrete structures. Among other effects, moisture levels determine the risk of corrosion attack occurring on cast-in steel and reinforcement and the rate of deleterious mechanisms such as alkali-aggregate reaction. At the same time, a long-term ageing effect caused by drying-out of the cement matrix in concrete will be evident and the result will be reduced strength. A combination of dry and wet concrete may cause differential shrinkage which in turn may well lead to cracking.

A balanced and stable moisture level would seem to be desirable, but cannot be achieved because the structural members are usually massive and are subject to different environments. In addition, concrete moisture content also affects the results of many tests concerning concrete property. For example, moisture variations affect testing performance as the speed and penetration ability of acoustic and electromagnetic pulses used in modern techniques are strongly dependent on this factor. The criteria used in evaluating electrochemical test results are similarly affected by moisture (e.g., oxygen availability). It may be said that any advances in non-destructive testing methods will be dependent on the ability to determine the moisture condition of massive concrete members on-site and the ability to use this information in processing measurement data.

Detecting and monitoring moisture content in concrete structures is difficult with present sensing techniques. Two techniques—neutron meter and microwave measurement—have been proposed for detecting/monitoring moisture content in hardened concrete and are described, respectively, in Bonin et al., Nuclear Technology, 95(3), 337–348 (1991); and Al-Qadi, J. Testing and Evaluation, 21(1), 43–50 (1992). The neutron meter technique involves radioactive material and therefore, its safety is a serious concern in practical applications. The microwave technique has serious matrix effect in concrete moisture detection. The detected signal of this technique is affected by surface smoothness, air void content, concrete type and structure, etc.

Moisture sensors based on detecting electric property, such as capacity and resistance, are inappropriate for concrete moisture monitoring because the electrode of the sensor can corrode in the corrosive environment inside the concrete. In addition, the sensing element of these electric property based sensors normally cannot survive in the high alkalinity cement mortar.

Figure 11:
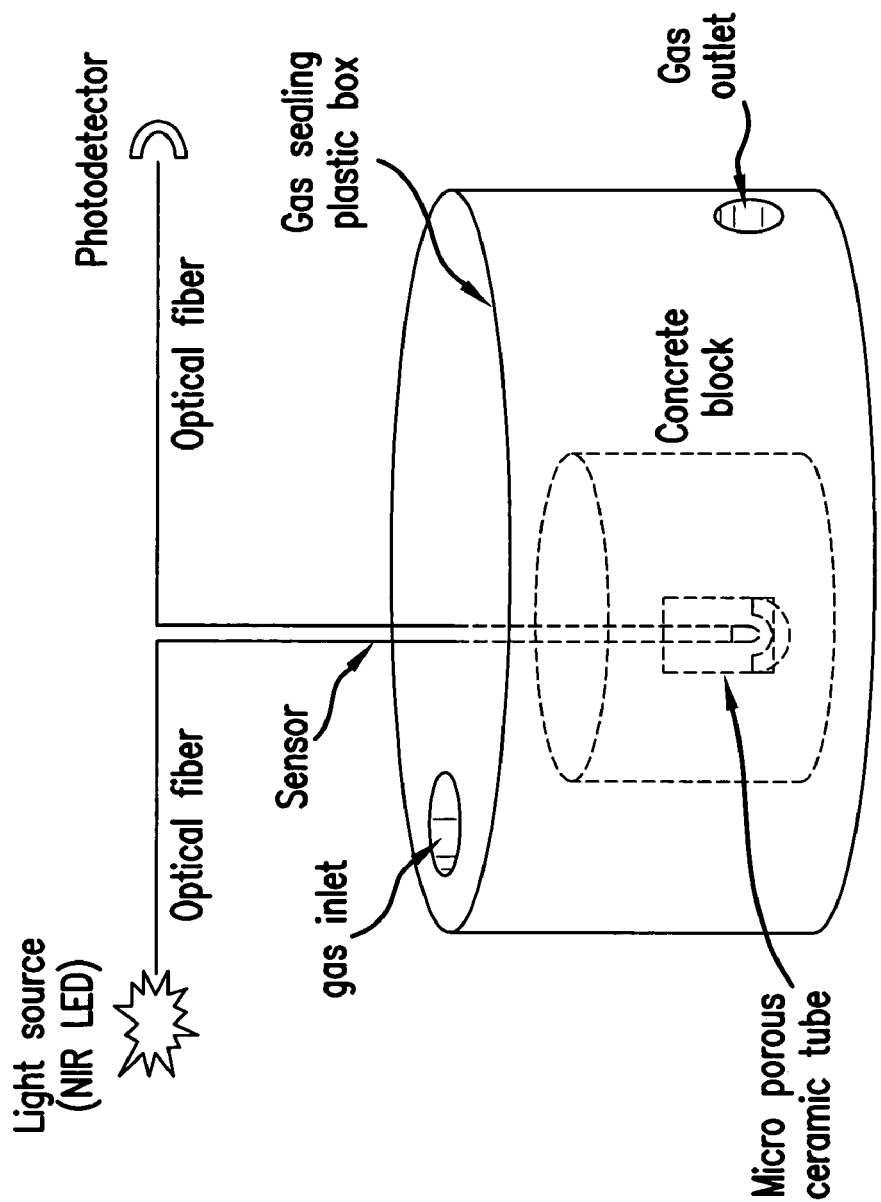
FIG. 11 is a block diagram illustrating an experimental setup for testing an optical fiber moisture sensor according to an embodiment of the present invention.

A sensor of the present invention having the same structure as that used for soil humidity sensing described above was fabricated. The coated bent fiber probe was further sealed within a round button micro porous ceramic tube. This ceramic tube packed bent fiber probe was then buried inside a concrete block at the time of making the concrete block from cement. After the concrete hardened, the concrete block was put into a gas sealing plastic box with gas inlet and gas outlet ports opened on the wall of the box as shown in FIG. 11. To test the sensor's response to moisture change in the concrete block, dry air gas was first flowed through the box to dry the concrete block.

Figure 12:
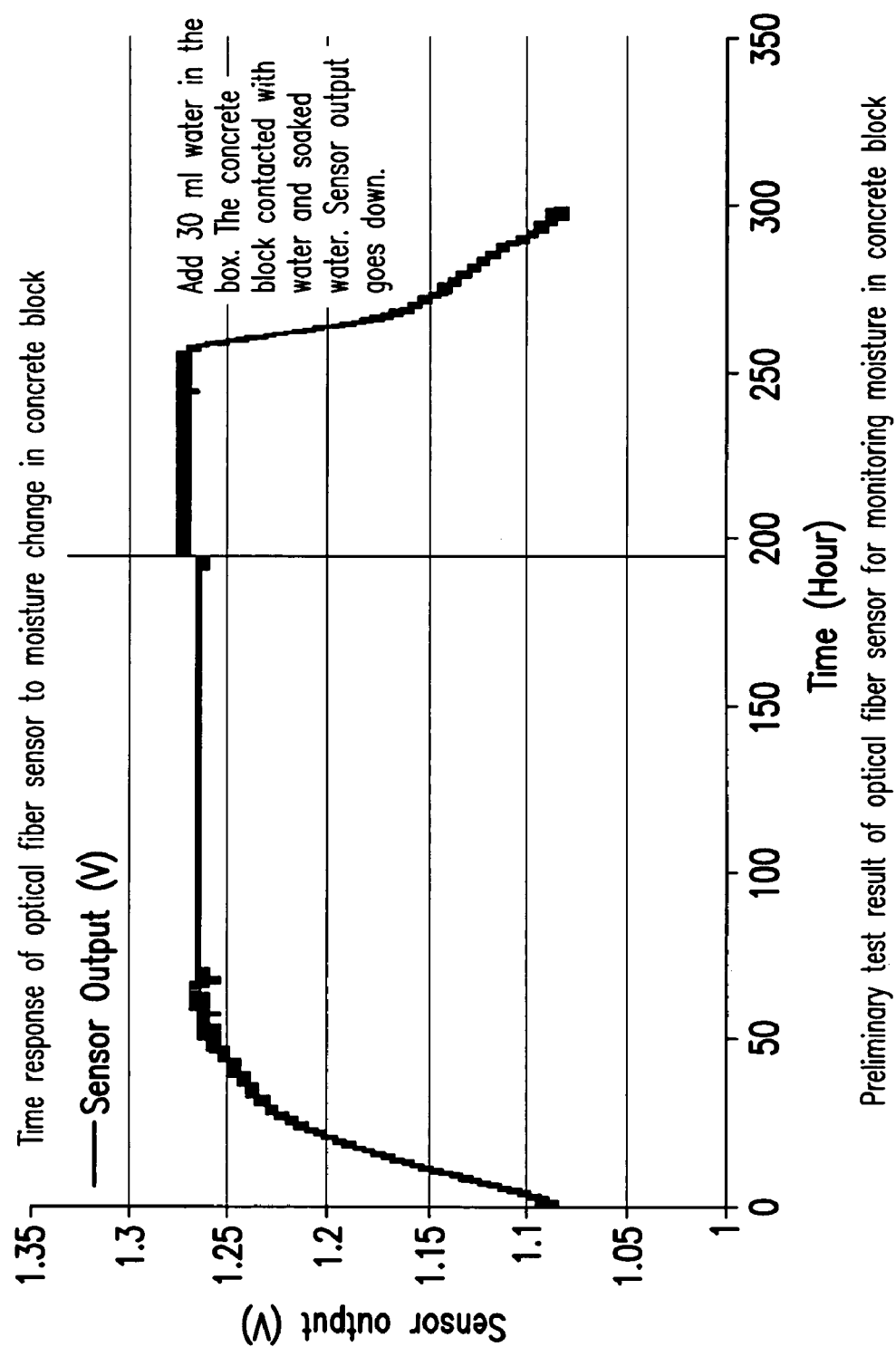
FIG. 12 is a graph plotting results of the experimental setup shown in FIG. 11 for testing the optical fiber moisture sensor according to an embodiment of the present invention.

As the concrete was drying, the bent probe guides more light to the detector and the sensor's output signal in voltage increased with time (as shown in FIG. 12). After more than 50 hours, the moisture content inside the concrete block equilibrated with the moisture content in the air and the output signal of the sensor stabilized. After more than 10 days, the dry-air flow was stopped, and 30 ml of water was added into the box. The concrete block absorbed water and the moisture content inside the block increased. The output signal of the sensor in voltage decreased with the increase of moisture inside the concrete block (as shown in FIG. 12). The results of this test clearly shows that the sensor of the present invention can be used for applications involving monitoring moisture content in concrete structures.

V. Exemplary Implementations

As detailed above, the present invention is directed to a porous sol-gel silica polymer coated on an optical fiber core that forms the transducer of an optical fiber moisture sensor. That is, as will be apparent to those skilled in the relevant art(s) after reading the description herein, the present invention is aimed at an optical fiber moisture sensor comprising a light source (e.g., near infrared light emitting diode or the like), a photodetector (e.g., photo diode detector or the like) and an optical fiber situated between the light source and the photodetector, wherein the fiber has a fiber core portion coated with a porous sol gel silica layer. In an embodiment, the fiber core portion of the optical fiber is about 0.5 to 2 centimeters (cm) long.

In alternate embodiments, the fiber core may be straight or bent. In embodiments where it is bent, the fiber core can be bent in a "U", "S" or other like shape.

In alternate embodiments, the light source (e.g., near infrared light emitting diode or the like) emits radiation having a wavelength longer than 400 nm (e.g., 500 nm to 700 nm).

In an embodiment, as will be appreciated by those skilled in the relevant art(s) after reading the description herein, the photodetector (e.g., photo diode detector or the like) of the present invention's optical fiber moisture sensor converts a light intensity signal to an electric signal and operates on an evanescent wave light scattering (EWLS) principle.

In alternate embodiments, as will be appreciated by those skilled in the relevant art(s) after reading the description herein, the optical fiber moisture sensor of the present invention is used to measure moisture content in a gas phase or moisture level in a gas phase present in indoor air, outdoor air, soil, concrete or gas stream.

VI. Conclusion

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. Thus, the present invention should not be limited by any of the above-described exemplary embodiments, but should be defined only in accordance with the following claims and their equivalents.

What is claimed is:

1. A method for preparing an optical fiber for use as a transducer in a moisture sensor, comprising the steps of:
   (a) polishing the two ends of an optical fiber;
   (b) applying a heat source to a portion of said optical fiber in order to remove the cladding layer of said portion;
   (c) soaking said portion of said optical fiber in a first solution in order to wash off any organic material possibly sticking on the surface of said portion of said optical fiber;
   (d) soaking said portion of said optical fiber in a second solution until the surface hydroxyl groups of said portion are activated; and
   (e) coating at least said portion of said optical fiber with a porous sol-gel silica solution.

2. The method of claim 1, wherein said first solution is a $K_2Cr_2O_7/H_2SO_4$ solution.

3. The method of claim 2, wherein said soaking step (c) is performed for at least 30 minutes.

4. The method of claim 1, wherein said second solution is a NaOH solution.

5. The method of claim 4, wherein said second solution is at least a 2 M NaOH solution.

6. The method of claim 5, wherein said soaking step (d) is performed for at least 12 hours.

7. The method of claim 1, further comprising the steps of: cooling said optical fiber to room temperature prior to said soaking step (c); and
   rinsing said portion of said optical fiber with de-ionized water both prior to and after said soaking step (d).

8. The method of claim 1, further comprising the step of: refrigerating said optical fiber coated with said sol-gel silica solution for at least 12 hours.

9. The method of claim 1, further comprising the step of bending said portion of said optical fiber during said applying step (b).

10. The method of claim 9, wherein said portion of said optical fiber is bent into a "U" shape.

11. The method of claim 9, wherein said portion of said optical fiber is bent into an "S" shape.

12. The method of claim 1, wherein said coating step (e) is accomplished by dipping said at least said portion of said optical fiber in said porous sol-gel silica solution.

13. The method of claim 1, wherein said portion of said optical fiber is about 0.5 to 2 cm long.

14. The method of claim 1, wherein said sol-gel silica solution is prepared by hydrolyzing a silicate ester with water using a catalyst.

15. The method of claim 14, wherein said silicate ester is selected from the group consisting of tetramethyl orthosilicate and tetraethyl orthosilicate.

16. The method of claim 14, wherein said catalyst is a mineral acid catalyst.

17. The method of claim 1, further comprising the step of:
   (f) coating said portion of said optical fiber with a thin layer of silicone rubber solution.

18. The method of claim 17, wherein said coating step (f) comprises the steps of:
   dipping said portion of said optical fiber in a silicone rubber coating solution; and
   air drying said optical fiber for at least 24 hours.

19. The method of claim 17, wherein said silicone rubber coating solution is prepared by the steps of:
   preparing a mixture comprising a silicon elastomer and a curing agent; and
   diluting said mixture with toluene.

20. The method of claim 1, further comprising the step of:
   applying a second coating to said portion of said optical fiber, the second coating being a permeable protective coating, wherein said second coating is made from the group consisting of: permeable polymers, permeable plastics, permeable thermoplastics, permeable polyurethanes, and permeable gels.

* * * * *